(12) United States Patent
Krause

(10) Patent No.: US 6,435,025 B1
(45) Date of Patent: Aug. 20, 2002

(54) APPARATUS FOR DETERMINING A PHYSICAL VARIABLE OF A LIQUID OR SOLID MEDIUM

(75) Inventor: Michael Krause, Steinen (DE)

(73) Assignee: Endress + Hauser GmbH + Co., Maulburg (DE)

( * ) Notice: Subject to any disclaimer, the term of this patent is extended or adjusted under 35 U.S.C. 154(b) by 0 days.

(21) Appl. No.: 09/638,421

(22) Filed: Aug. 14, 2000

(30) Foreign Application Priority Data

Sep. 7, 1999 (EP) .............................. 99117605

(51) Int. Cl.[7] .............................................. G01F 23/00
(52) U.S. Cl. .................................... 73/304 C; 73/290 R
(58) Field of Search ........................... 73/290 R, 304 R, 73/53.01, 53.06, 53.07, 54.01, 304 C

(56) References Cited

U.S. PATENT DOCUMENTS

| | | | |
|---|---|---|---|
| 3,847,020 A | 11/1974 | Jurschak | |
| 3,916,689 A | * 11/1975 | Donnelly | .................. 73/304 C |
| 4,733,560 A | * 3/1988 | Dam | .................. 73/304 C |
| 5,052,223 A | 10/1991 | Regnault et al. | |
| 5,187,444 A | 2/1993 | Kumada et al. | |
| 5,361,070 A | 11/1994 | McEwan | |
| 5,507,178 A | * 4/1996 | Dam | .................. 73/61.49 |
| 5,955,659 A | * 9/1999 | Gupta et al. | .................. 73/54.01 |

FOREIGN PATENT DOCUMENTS

| | | |
|---|---|---|
| DE | 29701436 | 5/1997 |
| EP | 0 038 078 | 10/1981 |
| EP | 0351700 | 1/1990 |
| GB | 2 040 472 | 8/1980 |
| JP | 57082731 | 5/1982 |
| WO | WO 96/04123 | 2/1996 |

* cited by examiner

Primary Examiner—Hezron Williams
Assistant Examiner—Katina Wilson
(74) Attorney, Agent, or Firm—Bose McKinney & Evans LLP

(57) ABSTRACT

The object of the present invention is to propose an apparatus for determining a physical variable of a medium (2) in which the formation of deposits or buildups of the medium (2) on a subelement (4) of the apparatus (1) which comes into contact with the medium (2) is reduced or avoided.

For this purpose, at least the subelement (4) is provided with a microstructured surface layer (7).

11 Claims, 1 Drawing Sheet

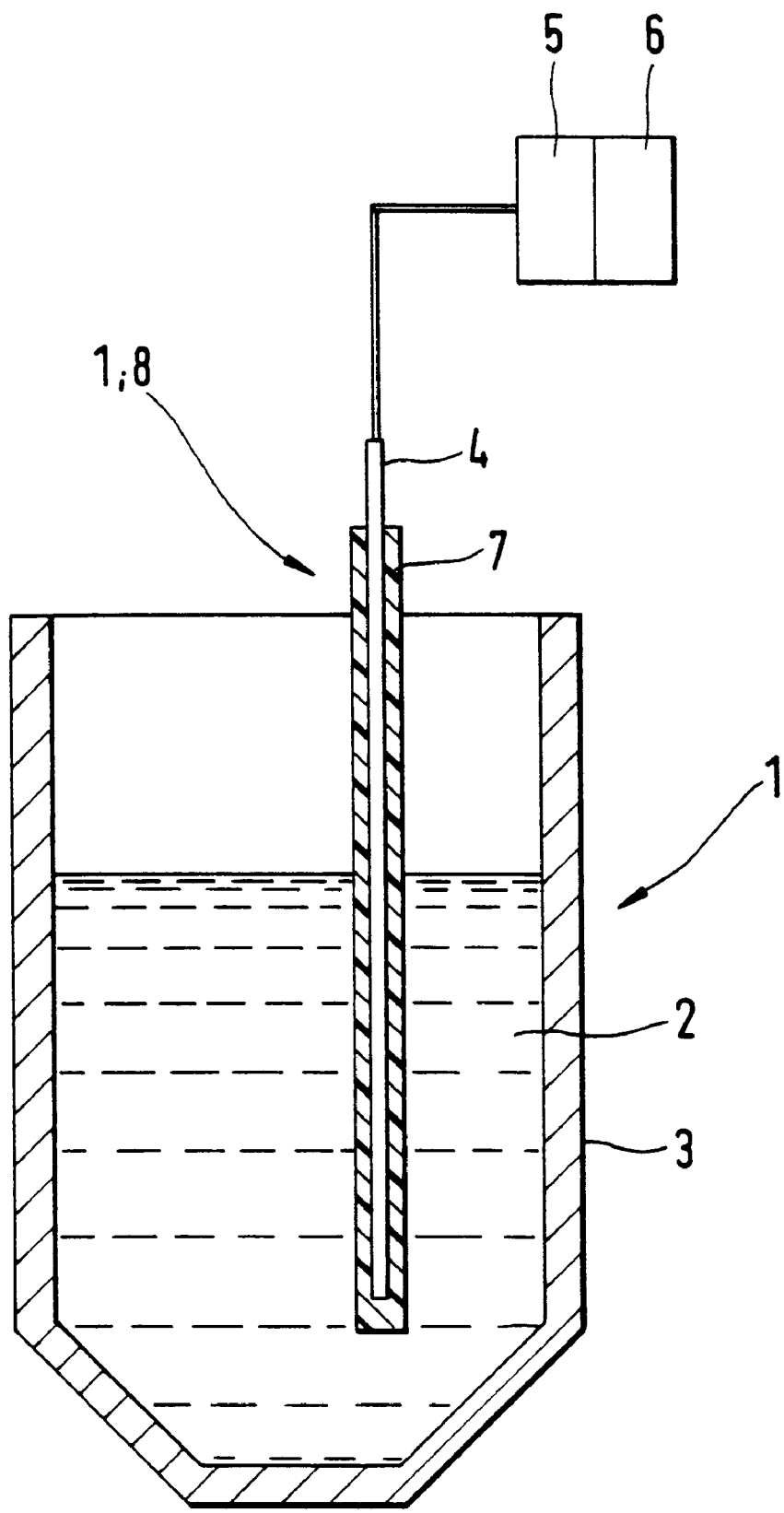

APPARATUS FOR DETERMINING A PHYSICAL VARIABLE OF A LIQUID OR SOLID MEDIUM

FIELD OF THE INVENTION

The invention relates to an apparatus for determining a physical variable of a liquid or solid medium in a container or in a vessel.

BACKGROUND AND SUMMARY OF THE INVENTION

A wide variety of types of sensors are used for determining physical measured variables. In applications in which at least a subelement of the sensor is in direct or indirect contact with the medium to be measured, there is the risk of build-ups forming on the corresponding sensor element. These build-ups impair the measuring accuracy or the function of the sensor in some cases quite considerably.

The invention is based on the object of proposing an apparatus in which the formation of build-ups on the sensor is reduced.

The object is achieved by the apparatus comprising a plurality of subelements, at least one subelement coming indirectly or directly into contact with the liquid or solid medium, and the at least one subelement having a microstructured surface layer. The microstructured surface layer prevents or reduces the formation of deposits on the sensor. Furthermore, a surface film is prevented from forming on the corresponding subelement of the sensor where there is contact with a viscous medium, for example honey.

The reason for the low formation of deposits is to be seen in the great reduction in the forces of adhesion between the sensor element and the medium due to the surface roughness of the sensor element. Even if a deposit forms, it can be easily removed again subsequently on account of the low forces of adhesion. In addition to the consistently good measuring accuracy, an important side-effect of this, as it were, self-cleaning surface structure is the increased service life of the sensor. Consequently, in addition to the (self) cleaning function, the microstructured surface also assumes a protective function.

According to an advantageous development of the apparatus according to the invention, the microstructured lay applied as a surface coating to the at least one subelement. It is preferred here, because of the simplicity of application, for the surface coating to be a layer of varnish or paint which has been applied to the least one subelement. It is also possible, however, to apply the surface layer by a different production technique. As an example, mention may be made here of vapor deposition.

One advantageous embodiment of the apparatus according to the invention proposes that the microstructured surface has elevations and depressions, the distance between the elevations lying in the range from 5 to 200 $\mu$m and the height of the elevations lying in the range from 5 to 100 $\mu$m. EP 0 772 514 B1 discloses in detail how the microstructured surface may be formed.

The apparatus according to the invention can preferably be used in the field of continuous level measurement or limit-level measurement. Used here are measuring systems which measure different physical variables and derive the desired information on the filling level from the variables measured. In addition to mechanical feelers, capacitive, conductive or hydrostatic measuring probes are used, as well as detectors which operate on the basis of ultrasound or microwaves. Less critical of course are sensors which do not come into direct contact with the product, although contaminations may also occur on microwave antennas for example, which are arranged above the product to be measured. In the case of other types of sensor which are immersed into the product for the purpose of measured value acquisition, the formation of deposits is usually particularly critical.

The formation of deposits is, however, problematical in any event in the case of capacitive sensors and TDR sensors. An arrangement for the capacitive level measurement of a medium arranged in a non-conductive container is disclosed for example by DE 38 24 231 C2. As a further example of capacitive sensors, mention may be made of the MULTICAP level sensors, produced and sold by the applicant. When there are deposits or build-ups on the probe, that is to say the subelement which is in direct contact with the product, the measuring accuracy is affected considerably. Measuring errors of the order of approximately 5% occur.

In many fields of application, for example petrochemistry, chemistry and the food industry, highly accurate measurements of the level of liquids or bulk materials in containers (tanks, silos, etc.) are required. Therefore, use is made here increasingly of TDR sensors, in which short electromagnetic high-frequency pulses or continuous microwaves are injected into a conducting rope or rod probe and introduced by means of the probe into the container in which the product is stored. Incidentally, TDR stands as an abbreviation for Time Domain Reflectometry. Seen in physical terms, this measuring method utilizes the effect that part of the guided high-frequency pulse or of the guided microwave is reflected at the boundary layer between two different media, for example air and oil or air and water, because of the abrupt change (discontinuity) in the dielectric constants of the two media, and is returned via the probe into the receiving device. The reflected component is all the greater here the greater the difference in the dielectric constants of the two media. The distance from the boundary layer can be determined on the basis of the delay time of the reflected component of the high-frequency pulse or microwave. With knowledge of the distance when the container is empty, the filling level of the product in the container can be calculated.

It has been found that the measuring accuracy of TDR sensors is reduced relatively greatly by the formation of deposits. Consequently, measuring errors of up to approximately 5% also occur here. Incidentally, a TDR sensor which can be used in connection with the apparatus according to the invention is described in U.S. Pat. No. 5,361,070. As a further example, mention may be made of the TDR sensor LEVELFLEX, produced and sold by the applicant.

The level sensor may, however, also be a vibration sensor. For the purpose of level measurement, here the detuning of the resonant frequency of the vibration sensor which occurs as soon as the vibration rods of the vibration sensor come into contact with the product is used for the purpose of level measurement.

The formation of deposits is always critical in the case of vibration sensors when the build-ups do not form symmetrically on the two vibration rods. As an example of vibration measuring systems, mention may be made of the LIQIPHANT or SOLIPHANT, likewise produced and sold by the applicant.

It goes without saying—as already described elsewhere—that the microstructured surface is also advantageous in connection with an antenna which transmits sound, ultrasound or electromagnetic waves in the direction of the surface of the medium.

Seen quite generally, however, the apparatus according to the invention is not only suitable for measuring the filling level of a product in a container but also can be used in connection with any type of sensor which can measure any desired physical variables of a liquid or solid medium and comes into contact with the medium or is exposed indirectly to the influence of the medium during the measuring operation. The physical variables mentioned above may be, for example, the pressure, temperature, humidity, throughflow or mass throughflow of a medium. The microstructured surface of the sensor element which comes into indirect or direct contact with the medium has the effect of effectively avoiding or reducing adherence of the medium to the corresponding subelement of the sensor.

DETAILED DESCRIPTION OF THE DRAWING

The invention is explained in more detail on the basis of the single figure. FIG. 1 shows a capacitive sensor 1 for a continuous measurement of the filling level of a product 2 in a container 3 which is produced from a conductive material. The sensor 1 comprises a sensor element 4, in the case shown a rod-shaped probe 4, an evaluation unit 5 and a display unit 6. To be able to carry out a continuous level measurement within a predetermined region of the container 3, the rod-shaped probe 4 must extend over the entire region of the container 3 to be monitored. The rod-shaped probe 4 serves as the first electrode, while the wall of the container 3 forms the second electrode.

In the container 3 is the product 2, which may be a liquid or solid. The sensor element 4 is partially immersed in the product 2. To protect the sensor element 4 from the formation of deposits or to simplify cleaning of the sensor element 4 in the event of deposits forming, the sensor element 4 has a microstructured surface 7. In the case shown, it is incidentally a microstructured surface layer which has been applied to the sensor element 4, for example, in the form of a varnish. As already mentioned several times, the microstructured surface layer 7 greatly reduces the adhesive effect between the sensor element 4 and the product 2.

What is claimed is:

1. An apparatus for determining a physical variable of a liquid or solid medium in a container or in a vessel, comprising a plurality of subelements, at least one subelement coming indirectly or directly into contact with the liquid or solid medium, and the at least one subelement having a microstructured surface layer, the microstructured surface layer having elevations and depressions, the distance between the elevations lying in the range from 5 to 200 μm and the height of the elevations lying in the range from 5 to 100 μm.

2. The apparatus as claimed in claim 1, the surface layer being a layer of varnish or paint which has been applied to the at lease one subelment.

3. The apparatus as claimed in claim 2, the plurality of subelements being configured to determine at least the pressure, temperature, humidity or throughflow or mass throughflow of the medium.

4. The apparatus as claimed in claim 1, the physical variable being a filling level of a product in the container.

5. The apparatus as claimed in claim 4, the at least one subelement being the probe part of a capacitive sensor which comes into contact with the product for the purpose of level measurement.

6. The apparatus as claimed in claim 4, the subelement being vibration rods of a vibration sensor.

7. The apparatus as claimed in claim 4, the subelement being an antenna which transmits sound, ultrasound or electromagnetic waves in a direction of a surface of the medium, or the subelement being a waveguide which guides the electromagnetic waves in a direction of a surface of the product or introduces them into the product.

8. The apparatus as claimed in claim 1, the physical variable being the pressure, temperature, humidity or throughflow or mass throughflow of the medium.

9. The apparatus as claimed in claim 1, the plurality of subelements being configured to determine at least a filling level of a product in the container.

10. The apparatus as claimed in claim 2, the plurality of subelements being configured to determine at least a filling level of a product in the container.

11. The apparatus as claimed in claim 1, the plurality of subelements being configured to determine at least the pressure, temperature, humidity or throughflow or mass throughflow of the medium.

\* \* \* \* \*

UNITED STATES PATENT AND TRADEMARK OFFICE
CERTIFICATE OF CORRECTION

PATENT NO.    : 6,435,025 B1
DATED         : August 20, 2002
INVENTOR(S)   : Michael Krause It is certified that error appears in the above-identified patent and that said Letters Patent is hereby corrected as shown below:

<u>Title page,</u>
Item [56], FOREIGN PATENT DOCUMENTS, -- EP    772514 12/23/98 --

Signed and Sealed this

Fifth Day of November, 2002

*Attest:*

JAMES E. ROGAN
*Attesting Officer*  *Director of the United States Patent and Trademark Office*